United States Patent [19]

Grove

[11] Patent Number: 4,896,278

[45] Date of Patent: Jan. 23, 1990

[54] AUTOMATED DEFECT RECOGNITION SYSTEM

[75] Inventor: R. Curtis Grove, San Pedro, Calif.

[73] Assignee: Northrop Corporation, Hawthorne, Calif.

[21] Appl. No.: 217,587

[22] Filed: Jul. 11, 1988

[51] Int. Cl.$^4$ .................. G06F 15/46; G01N 29/04
[52] U.S. Cl. .................. 364/552; 364/507; 356/237; 340/679; 358/106; 250/563; 73/598; 73/600; 73/602; 73/619; 73/622
[58] Field of Search .................. 364/506–508, 364/550, 552; 73/598, 600, 602, 606, 618–622, 625; 250/306, 358.1, 562, 563; 358/139, 140, 199, 106; 356/237; 340/674, 679

[56] References Cited

U.S. PATENT DOCUMENTS

| | | | |
|---|---|---|---|
| 4,213,183 | 7/1980 | Barron et al. | 364/507 |
| 4,344,146 | 8/1982 | Davis, Jr. et al. | 364/552 |
| 4,403,294 | 9/1983 | Hamada et al. | 364/507 |
| 4,433,385 | 2/1984 | DeGasperi et al. | 364/552 |
| 4,484,081 | 11/1984 | Cornyn, Jr. et al. | 364/507 |
| 4,561,061 | 12/1985 | Sakamoto et al. | 364/550 |
| 4,587,617 | 5/1986 | Barker et al. | 364/507 |
| 4,663,727 | 5/1987 | Saporito et al. | 364/552 |
| 4,697,245 | 9/1987 | Kara et al. | 364/552 |
| 4,752,895 | 6/1988 | Sarr | 364/507 |

Primary Examiner—Parshotam S. Lall
Assistant Examiner—Brian M. Mattson
Attorney, Agent, or Firm—Terry J. Anderson

[57] ABSTRACT

A computer-based defect recognition system for the automatic detection of parts defects includes an inspection knowledge base which enables automated defect inspections based upon a variety of nondestructive imaging tests, particular parts under test, the particular zone and region of the part, and the types of nondestructive imaging tests used. The knowledge database also provides for automated defect recognition to be applied to a wide variety of parts using a variety of nondestructive imaging tests while enabling flexible testing of different classified zones and regions of each part using the part-specific, zone- or region-specific, imaging test-specific inspection criteria, image processing algorithms, and computation algorithms.

4 Claims, 8 Drawing Sheets

AUTOMATED DEFECT RECOGNITION SYSTEM

BACKGROUND OF THE INVENTION

The present invention relates to defect detection systems and particularly to systems for detecting defects in manufactured parts and other components that may fail under mechanical stress due to some inherent structural defect or anomaly. More particularly, the present invention relates to defect detection systems and methods for detecting defects in manufactured parts, which systems and methods employ a knowledge database storing image processing and computational algorithms and inspection criteria, all of which are part dependent.

Certain manufactured parts are subject to mechanical stresses under operating conditions which can cause a defective part to fail without warning, with often dangerous consequences. Defects in these manufactured parts, fabricated by layup, casting, lost wax, mold injection, superplastic forming processes and other types of processes, may be detectable as anomalies in the surface or in the structure of the finished manufactured part. Surface defects include cracks, pits and excessive porosity. Structural defects include unbonds and delaminations.

For quality control and assurance, manufactured parts are subject to part inspections having predefined acceptance criteria applied against suspect anomalies. Typically, an inspector visually inspects the manufactured part for certain anomalies, and if the visually found anomalies are outside the bounds of the acceptance criteria, then the anomalies are considered defects and the part is rejected.

In modern fabrication facilities, more and more parts are fabricated using automated tools and machines with increased through-put and quality. As more automation is applied to the fabrication and assembly of parts, manual inspection accounts for an increasing percentage of the total manufacturing costs; thus, limiting cost reductions afforded by modern automation. Also, inspectors, unlike machines, are subject to fatigue and human error. The cost of inspection and nondestructive evaluation of parts in industry is becoming a larger percentage of the total cost of many component parts and assemblies. For these reasons, it is desirable to automate the inspection process whenever economically feasible.

Certain manufactured parts have been subject to nondestructive visual inspection procedures to aid inspectors in their task.

At present, both radiographic and ultrasonic imaging inspection techniques are being used in the aerospace industry to inspect composite graphite assemblies or parts. Composite assemblies are subject to defects such as delaminations between graphite surface. The part under inspection is generally held rigid while transmit transducers and receive sensors are raster-scanned line-by-line across the part. The received energy may be formatted and processed to form a digital image represented by intensity-modulated pixels (picture elements) on a display screen.

Radiographic and ultrasonic testing are, in many ways, complementary, and hence are used in concert to interpret the condition of a part to a higher degree than can be achieved with each test separately. A greater magnitude of received radiographic energy through a particular region of a part indicates a low density region of the part. On the other hand, a large amount of sensed ultrasonic energy through the part generally corresponds to a relatively higher density region. Radiographic energy will resolve finer detail, but is unable to detect certain defects such as unbonding that is readily detected by ultrasonic testing.

Testing methods to date, even automatic methods, have not addressed the need for combining processing and analysis of complementary inspection methods on a part. Inspection and defect interpretation procedures vary between different nondestructive inspection methods, yet there remains much commonality between methods that can lead to utilization of combined inspection knowledge bases.

U.S. Pat. No. 4,484,081, Cornyn et al., discloses a method for automatic inspection of parts using particular image processing techniques whereby a digitized video frame of a part under analysis is subjected to a thresholding means that utilizes a histogram computation to determine an optimum, threshold level to produce a binary anomaly image, said image being further processed by a region growing means to define and label unique anomalies in the image.

The anomalies are then measured with respect to their size. Decisions are then made as to whether each such anomaly constitutes a rejectable defect based upon predetermined rejection inspection criteria. In so doing, the shape, size and orientation of the part are used to compute region statistics such as area, and width-to-length ratio. These region statistics are then compared to an acceptance criteria table, that is, a region analysis means, relative to the region statistics to determine if the anomaly is a rejectable defect.

Hence, Cornyn et al '081 is directed to a particular automated defect detection system using a particular image processing technique whereby anomalies are detected based upon a particular thresholding means and labeled based on a region growing means. Furthermore, Cornyn et al is directed to a particular rejection criteria table based upon the calculated parameters and statistics which are the area, width-to-length ratio, and proximity to other defects. The system therein disclosed may be well suited for automated inspection of a single particular part.

However, both assembled and component parts are manufactured in an infinite variety of shapes and assembled structures using a wide variety of different materials. Each particular assembly or component part may be better and more completely tested using several different types of nondestructive imaging tests which depict the part under test. Using different image processing techniques to process different digitized images and using a wide variety of different inspection criteria, the part may be further tested. There is, therefore, a need for a new defect recognition system and method.

SUMMARY OF THE INVENTION AND OBJECTS

There are several types of image processing techniques which can be applied to various parts to further enhance the detection of anomalies found under one nondestructive image test and perhaps unlikely to be found under another nondestructive imaging test. For example, a part could be tested using ultrasonic, X-ray or thermographic nondestructive imaging tests each perhaps better suited for the detection of certain respective types of anomalies than the other test. Additionally, each particular part under test may have certain inspection zones and regions which are more critical than other zones and regions. Variable zone and region inspection with different respective types of image processing techniques and test criteria could be used to further enhance the detection of critical anomalies. That is, different types of image processing techniques and procedures could be applied to feature one type of expected anomaly with respect to different zones and regions of the part. Further still, image processing techniques and procedures could be applied to different regions having different respective inspection criteria. Further still, inspection criteria used to accept or reject a part could be further enhanced by incorporating many different types of inspection parameters and statistics which are part, region and test dependent rather than merely based solely upon physical size. An anomaly, though having otherwise acceptably small size in terms of area with regard to one particular part or region of a part, may nevertheless be rejectable because the shape or geometry of the anomaly is within a predetermined class of rejectable anomalies for other parts, regions and imaging tests. That is, the anomaly having defects acceptable for one part or one region or using one imaging test, may be rejectable with respect to another part, region or imaging test. From the foregoing, if an inspection system were developed for each type of imaging test, for each zone on the part, for each region on the part, for each type of image processing technique, for each type of inspection parameter, or for each type of part, a large number of different inspection systems, one example of which is described by Cornyn et al '081, would be needed at a correspondingly large and prohibitive cost. These and other disadvantages are solved or reduced using the present invention.

An object of the present invention is to provide a versatile automated defect recognition system which processes anomaly images obtained from different nondestructive tests, using a variety of image processing techniques and combines the results.

A further object of the present invention is to provide a versatile automated defect recognition system which uses image processing techniques that are nondestructive test-specific, part zone-specific, and part-region specific.

Another object of the present invention is to provide a versatile automated defect recognition system which uses image processing techniques that are nondestructive test-specific, part-specific, and part zone-specific, to process digitized anomaly images, subject to specific computational processing and inspection criteria that are nondestructive test-specific, part-specific, part zone-specific, and part-region specific.

Still another object of the present invention is to provide a versatile automated defect recognition system which uses image processing techniques that process digitized anomaly images, subject to computational algorithms that are nondestructive test-specific, part-specific, part zone-specific, and part-region specific, to generate anomaly measurements and statistics, the latter of which are compared to specific test, part and part zone inspection criteria for the purpose of defect rejection determinations.

Yet another object of the present invention is to provide a versatile automated defect recognition system which uses image processing algorithms that are nondestructive test-specific, part-specific and part zone-specific, to process digitized anomaly images, subject to computational algorithms that are compared to specific test, part, part zone, and part region inspection criteria for the purpose of defect rejection determinations.

The present invention provides a computer based defect recognition system for the automatic detection of part defects in cases where one nondestructive inspection test alone is insufficient to assess the structural integrity of the part. The part may be either an integral component part or an assembly of component parts. The part is subjected to a series of nondestructive imaging tests, each of which involves scanning an energy emitter and energy receiver synchronously or asynchronously over the inspection area of the part under test. The energy emitter transmits energy through or incident to the inspection surface of the part, and the energy receiver senses and converts received energy into an analog electrical energy which is further converted into a digital word in order that computer image processing may be applied to analyze the condition of the part as experienced by the particular nondestructive test. Because of the scanning process, samples of the received energy are associated with discrete areas of the part, and may be reconstituted into a spatial digital image representing the effect of the particular test at each discrete area of the part.

In one test, for example, the part may be placed in an ultrasonic bath whereby pulses are transmitted by a scanned ultrasonic emitter through the part and are sensed by ultrasonic sensor located in the bath on the other side of the part and moving in synchronism with the emitter. The scanner electronically processes the sensed signals, providing a raster scan image of the part, which image is a pixelized raster scan with each pixel having a particular voltage or current level.

A second test may then be performed on the part. For example, the part may be placed in a radiation lead room and scanned with X-ray energy. An X-ray image intensifier or scanned solid-state sensor may then recover X-ray energy through the part under test. As in the first test, electronic conversion takes place and a raster scan image of the part is obtained, representing the effect of X-ray testing.

Although each test is designed to reveal particular information about the part quality and integrity, all tests considered in the present invention scan the energy emitter and energy receiver across identical areas of the part. The energy emitter, while being scanned over any one location, transmits its energy over a discrete area of the part surrounding and including the center of the scan location. Further, the energy receiver, while at the same scan location, receives emitted energy from this discrete area of the part surrounding and including the center of the scan location. Part quality information is obtained from this discrete area centered at the current scan location when an analog transducer associated with the energy receiver connects the received energy with a proportional voltage level. By well known analog-to-digital conversion techniques, the proportional voltage level is converted into a digital number for storage in a digital computing system.

Due to differing energy wavelengths of the two test energies and possibly due to differing scan methods, more or fewer samples or picture elements may be obtained from one test than from another. Nevertheless, each raster scan image may be communicated to a central computer or processor where the number and spatial locating of picture elements from the raster images of each of various nondestructive tests may be made identical using image processing methods such as replication or interpolation.

In addition to general purpose program storage, the computer is provided inspection criteria data files and codified inspection image processing programs, both of which combine to form a test, part, and part zone region-specific inspection knowledge data base. The inspection knowledge data base enables automated defect inspections based upon the particular part under test, the particular zone or region of the part, the type of nondestructive test performed, and the particular inspection criteria. Parts found to be defective are recorded as such in the memory of the computer, and the defect area is displayed for visual review by the computer operator. The inspection criteria data files comprise inspection criteria which are based upon and organized by part, part zone and nondestructive test and which pertain to anomaly parameters and statistics. The codified inspection image processing programs are special purpose image processing and computational algorithms are nondestructive test, part and part zone-specific. The term "specific" herein is defined to mean a specifically selected one of several of the image processing algorithms, computational algorithms or inspection procedures. For example, if an inspection comparison is test, part, and part zone-specific, the test, part, and zone of the part then specify which of the many comparison procedures is to be selected for that specific zone of that specific part under the specific nondestructive test.

Hence, the present invention provides a single central computer system enabling automated defect detection applied to a variety of parts and nondestructive imaging tests. Furthermore, the system enables flexible testing using inspection criteria, image processing and computation that is test, part, and part zone-specific to particular parts having predefined inspection zones for a particular nondestructive test. The inspection criteria can be based on a wide variety of defect features including area, shape, proximity to other anomalies, etc. The inspection criteria is related to the particular nondestructive test, part, and part zone. The herein disclosed automated defect recognition system avoids the problem of manual-intensive inspection of parts while enabling flexible automated detection of a wide variety of parts using different nondestructive tests. These and other advantages will become more apparent in the following description of the preferred embodiment and the accompanying drawings, of which:

DESCRIPTION OF THE DRAWINGS

FIG. 2 is a flow chart of the automated inspection process.

DETAILED DESCRIPTION OF THE PREFERRED EMBODIMENT

Figure 1:
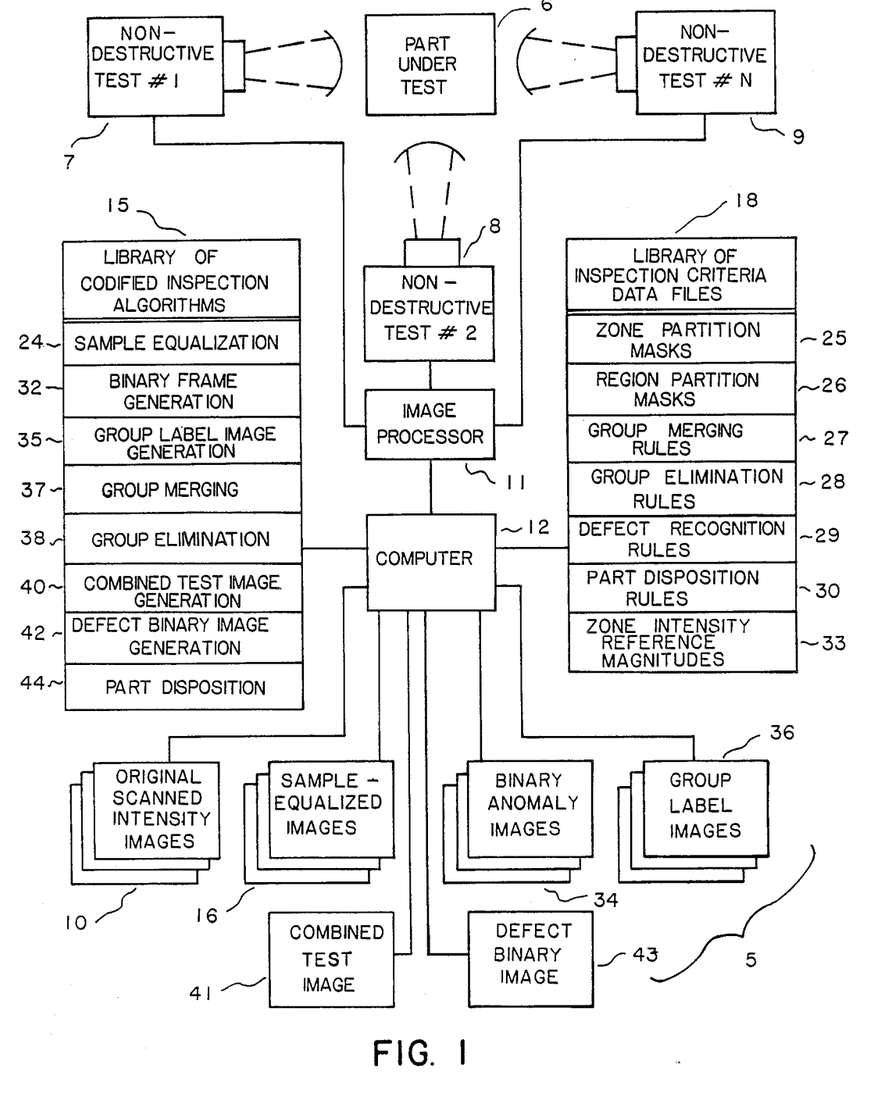
FIG. 1 is a system block diagram of an automated defect recognition system constructed in accordance with the present invention.

Referring to FIG. 1, an automated defect recognition system 5 is used to automatically detect defects of a part 6. The part 6 may be a single integral part or a composite assembly of various parts tested as an assembled part. The part 6 may be, for example, a graphite-epoxy laid-up assembled part which is well suited for nondestructive ultrasonic image testing and for other types of nondestructive imaging tests such as X-ray imaging or thermographic testing using infrared sensors.

Referring to both FIGS. 1 and 2 (FIG. 2 illustrates a flow diagram of the processes of the invention), a series of nondestructive imaging tests are performed by a set of scanners, 7 through 9 being illustrated (the number of different types of tests is not specifically limited in the invention, but in the preferred embodiment, would include at least three distinct nondestructive tests), which include excitation sources and sensors that each of which subject the part 6 to incident test energy across its test volume and sense and convert the recovered test energy from the part 6 to electronic signals of proportional magnitude. The scanners 7–9 format the electronic signals into full frame raster scan images having variable intensity pixels (picture elements) corresponding to the recovered test energy from each specific test at corresponding spatial locations on the part 6. The intensity pixels are digitized (i.e., converted to electrical digital numbers) corresponding to each pixel of the raster scan image. State-of-the-art systems prior to the present invention have used the heretofore described method on single nondestructive tests for visual non-automated inspection by converting the analog or digitized raster scan image to light intensity pixels for viewing on a CRT monitor.

Figure 3A:
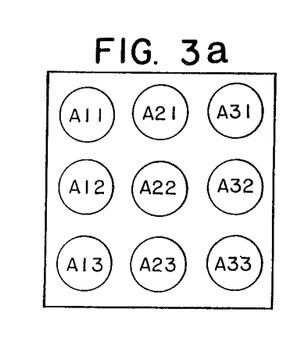
FIG. 3A depicts a specific area of a high resolution intensity-modulated image frame.
Figure 3B:
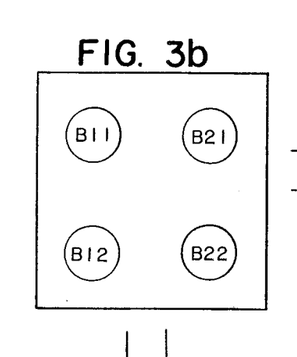
FIG. 3B depicts a specific area of a low resolution intensity-modulated image frame.

Scanners 7 through 9 communicate full frames of image data 10(a,b,c) to an image processor 11 controlled by a computer 12. An exemplary representation of an intensity modulated frame of image data is represented as an image in FIG. 3A. The designation for each intensity pixel, e.g., A21, represents the magnitude of the intensity at that spatial location. The image processor 11 performs various processes on images obtained from scanners 7 through 9 and on subsequently generated images 10(a,b,c) stored in computer 12 memory. Image processing algorithms to perform these procedures are obtained from a library of codified inspection procedures 15, accessible by computer 12. In the preferred embodiment, this access is by disk file retrieval. Due to differing scan methods performed by scanners 7 through 9, pixels obtained from one or more of these scanners do not necessarily correspond spatially and/or in density with pixels obtained from other of the scanners. An exemplary representation of intensity modulated images obtained from two different scanners is illustrated in FIG. 3A and FIG. 3B. It is seen that a different number of pixels are obtained from the two tests. An algorithm 24 from library 15, designated Intensity Image Sample-Equalization, re-processes image frames 10(a and b) from scanners 7 and 8 to obtain sample-equalized intensity images 16 having digitized pixels that correspond spatially to pixels of intensity image 10(c). This algorithm proceeds as follows:

1. Determine and select the image with the highest pixel density or resolution. (In FIG. 2, this is designated as intensity image 10(c). In FIG. 3, it would be FIG. 3A.) This image will not be modified, but the lesser-density test images 10(a and b) will be modified by relocating these pixels to correspond spatially to the image 10(c).

Figure 3C:
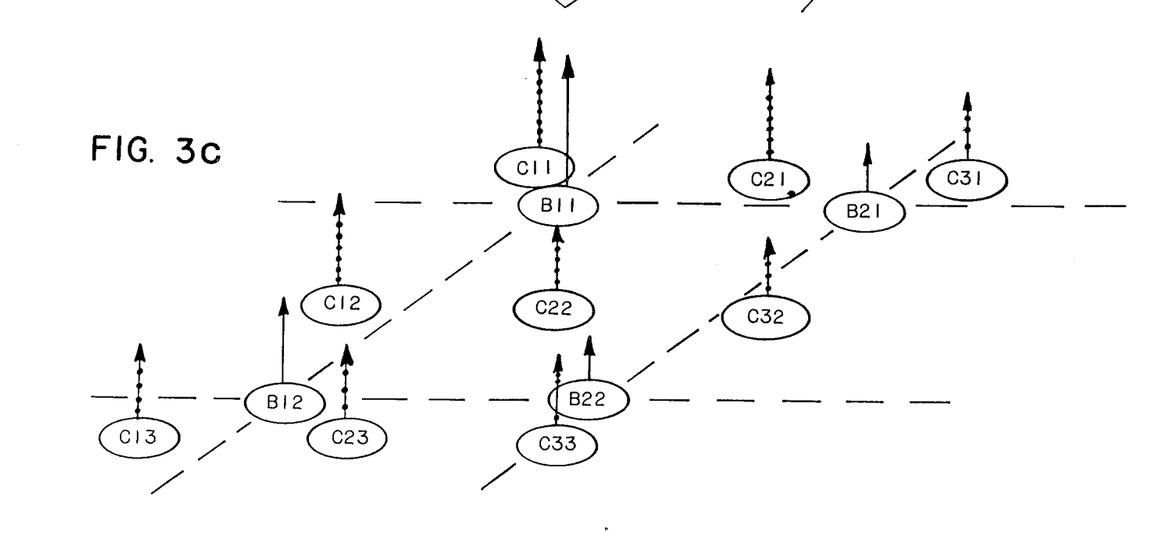
FIG. 3C depicts a perspective 3-dimensional view of the sample-equalization process.

2. Add and/or relocate pixels in the other test images (e.g., FIG. 3B) using an interpolation method well known in the state-of-the-art of signal and image processing:

a. Calculate the mathematical neighborhood intensity function by fitting a two-dimensional surface to the intensity magnitudes and locations of the pixels adjacent to and surrounding the proposed pixel location. Referring to FIG. 3C which is a perspective view of the image of FIG. 3B, solid arrows at the intersection of the dashed lines represent the four intensity magnitudes B11 through B22. Visualize a surface touching the tips of these arrows. This represents the neighborhood intensity function.

b. Calculate the intensity from the neighborhood intensity function at pixel spatial locations corresponding to the test image of step 1, and store those intensity values at these proposed pixel locations. This is illustrated in FIG. 3C as the dotted arrows emanating from the base plane. Their designations are C11 through C33, and they are co-located at A11 through A33, respectively. Their magnitudes (length of their arrows) are such that they just "touch" the surface of the neighborhood intensity function. (Note that the magnitudes of C11 through C33 are dependent on the magnitudes of B11 through B22, but not on the magnitudes of A11 through A33.)

Figure 3D:
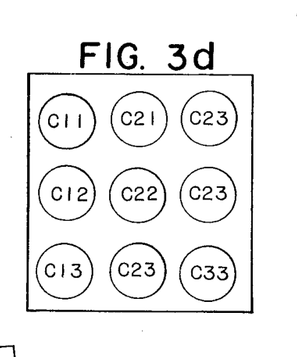
FIG. 3D depicts a sample-equalized intensity image derived from the image of FIG. 3B.

FIG. 3D illustrates the generation of a sample-equalized image for the scan of FIG. 3B wherein the sample-equalized image conforms in pixel location and density to the highest density image of FIG. 3A. This sample-equalization process allows data from different nondestructive tests to be spatially correspondent to provide a more complete nondestructive assessment of a part condition. Algorithm 24 thus constitutes a significantly novel ingredient of this invention, allowing many different nondestructive tests to be automatically evaluated in concert, both quantitatively and qualitatively, using identical spatial criteria.

Figure 4A:
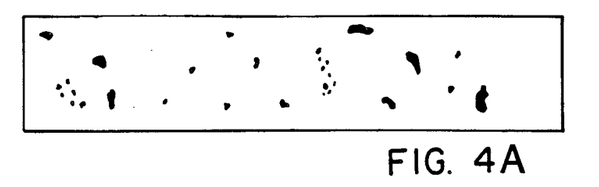
FIG. 4A depicts another sample-equalized image frame.

Also accessible by computer 12 is a library of inspection criteria data files 18. The library 18 includes inspection criteria such as part- and test-specific zone 25 and region 26 partition locations, and various inspection rules 27 through 30. Also stored in library 18 are zone intensity reference magnitudes 33 corresponding to the zone partition masks 25. This library 18 is also accessible, in the preferred embodiment, by disk file retrieval. In the preferred embodiment, a distinction is made between zones and regions. Refer to FIG. 4 for an exemplary description of zones and regions. FIG. 4A represents one of the set of sample-equalized intensity images. A zone, as depicted by way of example in FIG. 4B, e.g., Z1 or Z2, is a part- and test-specific area of the specific sample-equalized intensity image in which the criteria for detection of anomalies in areas and/or volumes on the corresponding part locations is constant for the given test, because the construction or makeup of the part in this zone is constant. On the other hand, a region, as depicted by way of example in FIG. 4D, e.g., R1 or R2, is a part-specific area on the image under which acceptance criteria remains constant. Zones and regions may completely or partially overlap. For example, a specific area may be very critical for the integrity of the entire part and be classified as R1. Zones Z1 and Z2, on the other hand, may encompass areas of region R1, since different detection criteria are required in these specific zones.

Figure 4B:
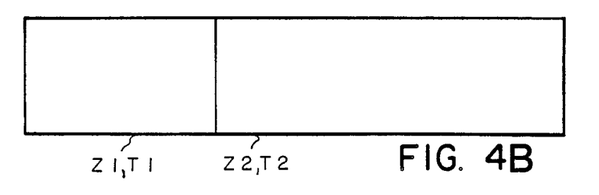
FIG. 4B depicts a zone overlay map.
Figure 4C:
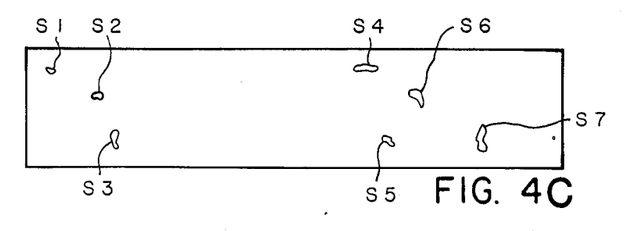
FIG. 4C depicts a binary frame image.
Figure 4D:
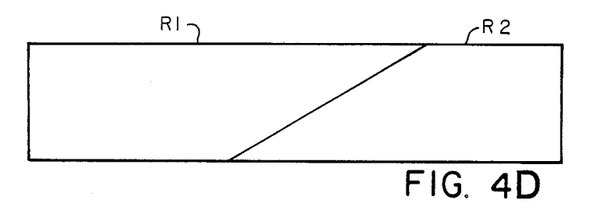
FIG. 4D depicts a region overlay map.
Figure 4E:
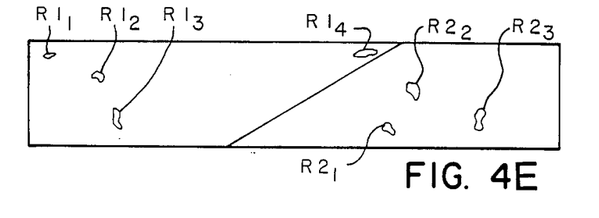
FIG. 4E depicts a binary frame image with suspect anomalies overlaid with a region overlay map.

A further algorithm from library 15, designated Binary Image Generation accesses specific zone mask 25(a,b,c) and corresponding test- and zone-specific intensity reference magnitudes 33(a,b,c) from library 18, one pair at a time, designated by way of example in FIG. 4B as (Z1, T1) or (Z2, T2), utilizing them to obtain a set of binary anomaly images 34(a,b,c) equal in quantity to the number of nondestructive tests performed. The designation "anomaly" refers to a suspect area that will subsequently, on the basis of further processing, either be declared defective or otherwise. The procedure is as follows: One test-specific zone mask 25 is applied to one of the set of sample-equalized intensity images 16. The function of the zone mask is as a logical AND function, i.e., only pixels overlaid with the zone mask are further considered at this step. The corresponding zone-specific intensity reference magnitude 33 is compared with each pixel intensity overlaid by the zone mask 25. If the pixel intensity is greater than the reference magnitude, a 1 or upper binary state is inserted into the corresponding binary frame image pixel location. Otherwise, a 0 or lower binary state is inserted. This completes the generation of the first binary frame image. FIG. 4C represents a resulting binary frame image wherein the pairs Z1, T1 and Z2, T2 have been applied to the image of FIG. 4A. The procedure continues until all test-specific zone masks have been applied to the current sample-equalized intensity image. The entire procedure is repeated with a new test-specific intensity image, a new set of test-specific zone masks and corresponding reference magnitudes. In this manner, one binary frame image is generated for each of the set of sample-equalized intensity images 16.

A further algorithm 35 from library 15, designated Group Labeling generates a group label image 36 for each binary frame image 34. The algorithm proceeds as follows: For each binary frame image, each pixel of upper binary state 1 is considered in turn. In the corresponding group label image, the first pixel is assigned a label of 1. Group label image pixels are also assigned a label of "1" whose corresponding upper binary state pixels are adjacent to the first pixel. Each of this second group of pixels is then considered in turn. All unassigned upper binary state pixels adjacent to pixels labeled 1 are also assigned a 1 label. When all label 1 pixels have been assigned, the next unlabeled pixel is assigned a 2 label. The procedure repeats, assigning all unlabeled pixels that are adjacent to label 2 pixels also to label 2. The algorithm continues until all pixels in the first group label image spatially corresponding to upper state binary frame picture elements have been assigned labels. The algorithm is then applied to each of the binary frame images in turn to produce corresponding sets of group label images.

A further algorithm 37 from library 15, designated Group Merging, accesses sets of test- and region-specific group merging rules 27 from library 18, each set of rules specific to a particular region of the specific group label image. To accomplish this, region masks 26, each in turn, are accessed from library 18 and applied to the group label image 36. The algorithm proceeds to apply these rules to pairs of groups in the currently considered region to decide whether the group pairs should be merged into one group. In the preferred embodiment of the invention, typical group merging rules are as follows:

1. Apply a region mask to the group label image.
2. Select one pair of the groups under the region mask. If a group lies within two or more regions, it is considered to be in the more critical of the regions.
3. Measure the greatest spanning distance L of the largest of the two groups. (Refer to FIG. 5 for a pictorial explanation of the described parameters.)
4. Next, measure the shortest gap distance C between closest pixels of the two groups.
5. If the ratio C/L is less than a threshold T, the two groups are merged into one group.

Figure 5:
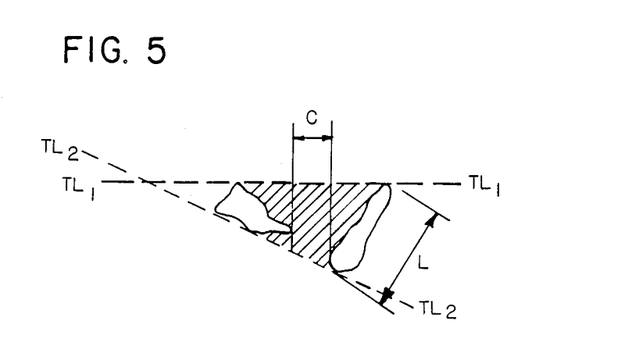
FIG. 5 depicts an isolated suspect anomaly.

The merging proceeds as follows:

1. An outer border encompassing the two groups is generated by introducing two lines TL1 and TL2, each tangent to each of the outer boundaries of the two groups. The extensions of these two lines may intersect beyond the composite boundary of the two groups.
2. Unlabeled pixels contained between the two tangent lines and the individual borders of the two groups (cross-hatched area in FIG. 5) are assigned the label of the lowest of the two labeled groups.
3. Finally, the pixels of the highest of the two labeled groups are reassigned labels of the lowest labeled group.

This procedure repeats for every pair of groups under this region mask in the group label image in order to merge groups that have a close proximity. The algorithm is applied to each of the region mask areas for this group label image, accessing test- and region-specific group merging rules from library 18 for each of the region masks. The algorithm then repeats for each of the group label images in turn.

Figure 6:
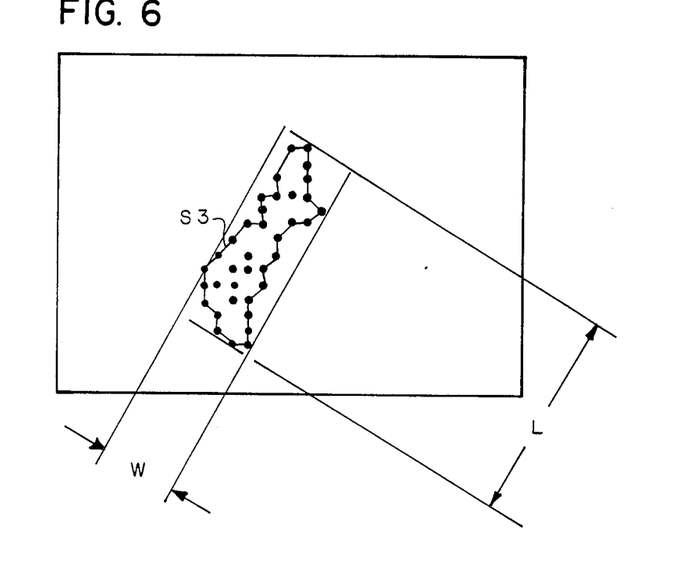
FIG. 6 depicts two close suspect anomalies.
Figure 7A:
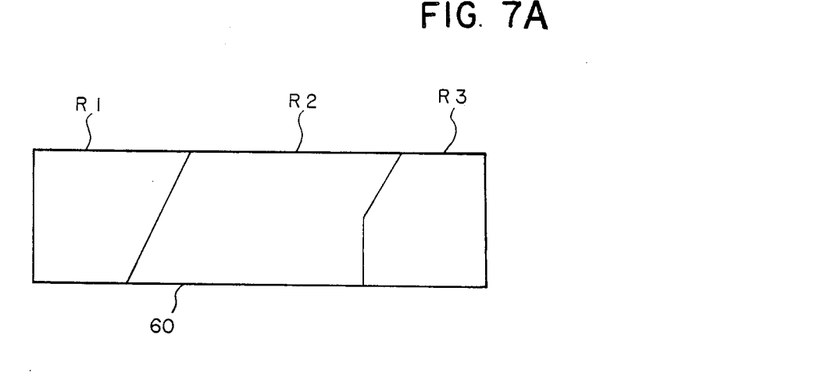
FIG. 7A depicts another region overlay map.
Figure 7B:
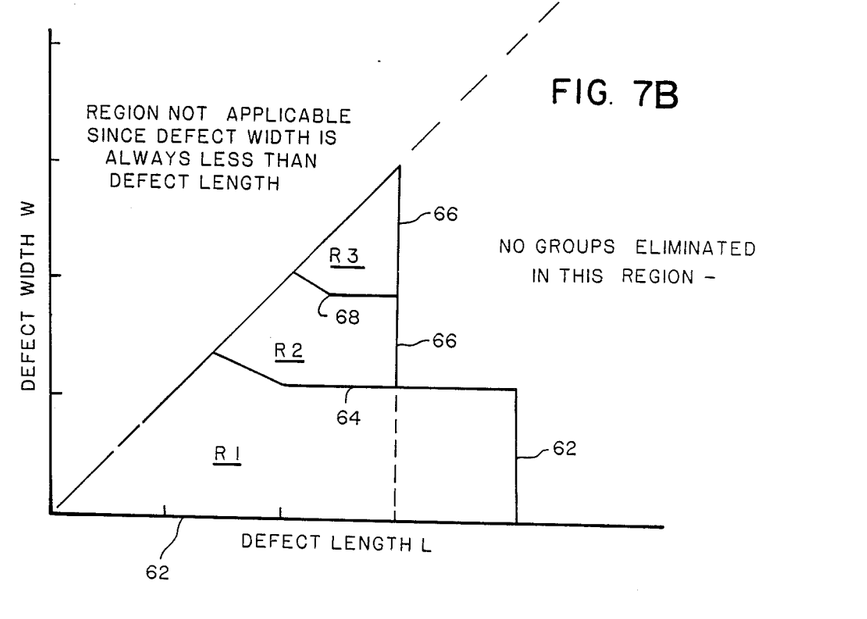
FIG. 7B depicts a region-based graphic accept/reject chart.

A further algorithm 38 from library 15, designated Group Elimination, accesses sets of test- and region-specific group elimination rules 28 from library 18, each set of rules specific to a particular region of the group label image. The algorithm proceeds to apply these rules to individual groups in the currently considered region to decide whether the group should be eliminated. To accomplish this, region masks, each in turn, are accessed from library 18 and applied to the group label image. In the preferred embodiment of the invention, typical group elimination rules are as follows:

1. Measure the greatest spanning distance L of the group, and note the orientation of L. (Refer to FIG. 6 for a pictorial explanation of the described parameters.)
2. Measure the spanning distance W perpendicular to L.
3. Apply the particular group elimination rule to the two parameters L and W to determine if that group will be eliminated. (Refer to FIGS. 7A and 7B for an exemplary graphic description of region-specific group elimination rules. In FIG. 7B, if L and W, for a given group, fall within the applicable area R1, R2 or R3, then that group will be eliminated from the group label image.)

The elimination is accomplished by unlabeling every labeled pixel of that group. This procedure repeats for every group under this region mask in the group label image in order to eliminate groups that are too small. The algorithm is applied to each of the region mask areas for this group label image, accessing test- and region-specific group elimination rules 28 from library 18 for each of the region masks. The algorithm then repeats for each of the group label images in turn.

A further algorithm 40 from library 15, designated Combined Test Image Generation, generates a combined test image 41 containing pixel word lengths greater or equal to the number of nondestructive tests. In this combined test image, at any pixel, corresponding pixels from each of the group label images $35(a,b,c)$ are examined. Each bit position of the combined test image pixel corresponds to a particular nondestructive test. The bit position will be in an upper state, or 1, if the corresponding group label image pixel has a value other than zero (it has been assigned a group label number). Conversely, it will be in the lower 0 state if the corresponding group label image pixel has a zero value.

A further algorithm 42 from library 15, designated Defect Binary Image Generation, by accessing test- and region-specific defect recognition rules 29 and region masks 26 from library 18, proceeds to generate binary states in each pixel of each region of a defect binary image 43. In the preferred embodiment of the invention, defect binary image generation proceeds as follows:

1. Apply a region mask to the combined test image.
2. For each pixel underlying the region mask, apply the region-specific defect recognition rule to that pixel. This rule, in the preferred embodiment, is a look-up table that converts the pixel value in the combined test image to a binary state that is inserted in the corresponding spatial location in the defect binary image. The correspondence between combined test image pixel value and defect binary image pixel binary state as stored in the look-up table is predetermined from knowledge of the effect of the various nondestructive tests on the part in that region.
3. Repeat the two previous steps for each region mask of the part.

Step 2 of algorithm 42 provides a crucial step to the invention. What is implied in step 2 is that at each pixel location in the combined test image 41 where the result of each of the nondestructive tests 7 through 9 is coded, the combined effect of these tests on the particular region (defined by the region mask 26) will specifically result in a locally defective or healthy condition at that pixel location. The look-up table embodied in the defect recognition rules 29 is -part and -region specific. Therefore, the invention automatically accomplishes what heretofore required tedious examinations by inspectors attempting to correlate the results of different nondestructive tests scanned under different conditions, some of which may have been performed automatically by various equipment as described in the literature in recent years.

A final algorithm 44 from library 15, designated Part Disposition, by accessing part- and region-specific disposition rules 30 and region masks 26 from library 18, proceeds to categorize each region of the part in turn, according to three disposition categories:

1. acceptable
2. repairable and salvageable
3. rejectable

In the preferred embodiment, this categorization takes place as follows:

1. Apply a region mask to the defect binary image 43.
2. Count the number of picture elements of upper binary state underlying the region mask. Apply the part- and region-specific part disposition rule to categorize the region into one of the above three categories.

This rule, in the preferred embodiment, is a look-up table that converts the upper state binary pixel count from the specific region of the defect binary image to a region category that is inserted in a part disposition table 45 in computer memory.

3. Repeat the two previous steps for each region mask of the part.

Step 2 of algorithm 44 is also a crucial step in the invention. While algorithm 42 identifies defective or healthy pixel locations in the combined test image 41 to produce the defect binary image 43, algorithm 44 recognizes that a full assessment of the acceptability or disposition of the part must be made on a more global basis within each specific region. The look-up table embodied in the part disposition rules 30 therefore stores the number of defective pixels in each specific region of the part under test that will constitute acceptance, rejection, or in many cases, the repairability and salvageability of the part. It should be kept in mind that all parts are not potentially salvageable, but on the other hand, the invention allows for the real possibility of automatically determining this.

Finally, there are many possible ways to dispose of the part after the foregoing automated defect recognition. In the preferred embodiment of the invention, the part disposition after inspection in this manner.

1. If all regions are acceptable, the part is acceptable.
2. If one or more regions are repairable and salvageable, and no region is rejectable, the part is to be repaired and salvaged.
3. If any region is rejectable, the part is rejected.

It becomes obvious that other accept/reject strategies are applicable while still providing the spirit and intent of the present invention. From the foregoing, the present invention provides a computer-based automatic defect recognition system characterized by part, zone, region, and test specific image processing, computation and inspection. It should be understood that different partitioning schemes may be used, for example having several different zone and region overlay maps. The difference between the use of the terms region or zone, as used herein, clearly differentiate between zone image processing and region inspection, even though the terms generally define a partition area. It should also be understood that processing in the present invention includes modifications of various processing steps heretofore described, and the omission of certain processing steps heretofore described, such as intensity threshold levels. Each form of nondestructive inspection, be it X-ray, ultrasonic, thermal or other, requires a different interpretation of the recovered electric image signals, and thus a different set of image processing algorithms and criteria. However, in all of these cases, the method heretofore described may be seen to include the automated recognition of defects in parts subjected to these various forms of nondestructive test and inspection.

Additionally, the computer may be distributed into hardware modules or peripherals, all under control of one central supervisory processor, said modules designed to efficiently perform the process they were designed for (e.g., dedicated pipeline or array processing for manipulation of image pixel data) so that dedicated hardware systems that may only vaguely resemble a computer system can be used to carry out the invention. Even though those skilled in the art may invent and conceive different automatic defect recognition system designs and modifications, those designs and modifications may nevertheless represent applications and principles within the spirit and scope of the present invention as defined by the following claims, of which:

What is claimed:

1. A method for defect recognition of a part tested by a plurality of nondestructive scanning image tests, comprising the steps of:

selecting a plurality of tests to be performed, employing a digital computer employing digital words of bit length equal to or greater than said plurality of tests, recording which one of said tests is used, recording the number of tests to be performed, assigning each test a unique test number, defining a test surface on said part, recording a scan aperture area for each test, scanning said part under each test with constant energy transmitted from an energy emitter into successive discrete areas on said test surface of said part, recovering successive portions of said constant energy transmitted into said successive discrete areas on said test surface with an energy receiver, forming an intensity-modulated frame image comprising a two-dimensional projection of received portions of said constant energy from said test surface, one intensity-modulated frame image obtained from each of said set of tests and containing digital picture elements, each digital picture element corresponding in location on said frame image to locations of discrete areas on said test surface on which said part, each said digital picture element having an intensity value proportional to said portion of said constant energy received by said energy receiver from said discrete area, determining which subset of said set of intensity-modulated frame images has the largest quantity of digital picture elements, identifying one of said subsets as a highest density frame image, identifying which of said tests that produces a highest density frame image as a highest density test, identifying all of said frame images except the highest density frame image as lesser density frame images, processing each of the sets of intensity-modulated frame images other than the highest density frame image to form a set of corrected frame images, each of said sets of corrected frame images having said largest quantity of digital picture elements, whereby corresponding picture elements in each of said sets of said corrected frame images, will correspond in location on said processed frame image to locations of discrete areas scanned by the highest density test on said test surface on said part, partitioning each of the sets of corrected frame images and the highest density frame images into test-specific zones, wherein a test-specific zone is defined as a test-specific bounded area on a test-specific frame image, corresponding to a test-specific bounded area on said test surface of said part, storing zone-specific intensity reference magnitudes, said intensity reference magnitudes to be used for comparison with intensity values of frame image picture elements, processing each of the sets of corrected frame images and the highest density frame image to form a set of binary anomaly images, wherein each binary anomaly image picture element is defined to correspond spatially to a corrected or highest density frame image picture element if their location on their respective images correspond, each of said sets of binary anomaly images containing picture elements of an upper binary state that correspond spatially to recorded intensity magnitudes on the corrected or highest density frame images that exceed zone-specific intensity reference magnitudes, and containing picture elements of a lower binary state that correspond spatially to recorded intensity magnitudes on the corrected or highest density frame images that do not exceed zone-specific intensity reference magnitudes, processing each of the sets of binary anomaly images to form a set of group label images, wherein each group label image picture element is defined to correspond spatially to a binary anomaly image picture element if their locations on their respective images correspond, said group label picture element either being labeled or unlabeled, said labeled picture element being assigned a label from a label set, each label in said label set being ordered, wherein any two labels of said label set are ordered with respect to each other as lower ordered label and higher ordered label, said group label picture element being unlabeled if the corresponding binary frame image picture element has a lower binary state, and being labeled if said corresponding binary frame image picture element has an upper binary state, said label being identical to that of an adjacent group label picture element if both group label picture elements have spatially corresponding binary anomaly image picture elements of upper binary state, and said label being unique if no binary anomaly image picture elements spatially corresponding to adjacent group label picture elements have an upper binary state, designating all labeled group label picture elements having identical labels as a group, partitioning each of the group label images into regions, said partitioning being identical in each of said group label images, said regions being bounded areas comprising two-dimensional projections of specific bounded areas on said test surface of said part, storing test-specific and region-specific group merging rules, said rules to be used to automatically decide if two groups in a specific group label image will be merged into one labeled group in the group label image, and to decide which lower state picture elements separating said two groups will be assigned to said merged labeled group, applying test-specific and region-specific group merging rules to all groups in the set of group label images in order to merge groups in the set of group label images, wherein the merging of two groups is accomplished by reassigning unlabeled picture elements separating the two groups to the lower ordered label of said two groups and reassigning all labeled picture elements of the higher ordered label of said two groups to that of the lower ordered label of said two groups, storing test-specific and region-specific group elimination rules, said rules to be used for automatically deciding if a group in a specific group label image will be eliminated, applying test-specific and region-specific group elimination rules to all groups in the set of group label images to decide which of said groups will be eliminated, wherein the elimination of a group is accomplished by changing the label of each picture element in that group from a labeled to an unlabeled state, processing the set of group label images to form a combined test image containing digital picture element words of bit length greater than or equal to the quantity of tests in said set of tests, wherein each combined test image picture element is defined to correspond spatially to a group label image picture element if their locations on their respective images correspond, and wherein each bit position of each of said digital picture element words is assigned to the unique test number equal to said bit position, and the bit position will be in an upper state if the corresponding group label image picture element is labeled, and the bit position will be in the lower state if the corresponding group label image picture element is unlabeled, partitioning the combined test image into regions, said partitioning being identical to that performed on the set of group label images, storing region-specific defect recognition rules, said rules to be applied to the combined test image and to be used to categorize digital picture elements as either defective or non-defective, and applying region-specific defect recognition rules to all regions of the combined test image to generate a defect binary image, wherein each defect binary image picture element is defined to correspond spatially to a combined test image picture element if their locations on their respective images correspond, wherein said defect recognition rules are applied to each picture element of each region of the combined test image, and each picture element of the defect binary image will be placed in a lower binary state if said defect recognition rules applied to the spatially corresponding picture element in the combined test image categorize said picture element as defective, and said each picture element of said defect binary image will be placed in an upper binary state if said defect recognition rules categorize said spatially corresponding picture element in said combined test image as non-defective.

2. The method of claim 1 wherein the processing of each of the sets of intensity-modulated frame images to form a set of corrected frame images comprises:

determining high density subsets of picture elements in said highest density frame image whose locations correspond closest to the location of each picture element of said lesser density frame images, designating each picture element of said lesser density frame image whose location is closest to the location of each picture element of each of said high density subsets as the nearest neighbor of each of said subsets, determining low density subsets of picture elements in each of said lesser density frame images, wherein each picture element of each of said low density subsets is adjacent to said nearest neighbor picture element, calculating a continuous mathematical function for each of said low density subsets, each picture element magnitude and location of each of said low density subsets also being a subset of points of said function, further designating said function as a mathematical neighborhood function, calculating intensity magnitudes at each location in each of said lesser density frame images corresponding to locations of picture elements in said high density subset of said highest density frame image, said intensity magnitudes also being a subset of points of said mathematical neighborhood intensity function, and creating said corrected images corresponding to each of said lesser density frame images, wherein said calculated intensity values are assigned to locations corresponding to picture element locations in said higher density frame image.

3. The method of claim 1 further including the steps of:

storing part-specific and region-specific part disposition rules, said rules to be applied to said defect binary image to grade regions of parts into one of three disposition categories, wherein disposition category one implies that the part region is acceptable, and disposition category two implies that the part region is repairable and salvageable, and disposition category three implies that the part region is rejectable, and applying part-specific and region-specific part disposition rules to said defect binary image to grade each region of said part into one of three disposition categories.

4. The method as in claim 1 wherein said tests are selected from ultrasonic scanning, radiographic scanning, and thermographic scanning.

* * * * *